(12) United States Patent  
Jones (10) Patent No.: US 10,376,657 B2  
(45) Date of Patent: Aug. 13, 2019

(54) MEDICINAL VAPOR FILTRATION SYSTEM

(71) Applicant: Brendan Jones, Ashland, OR (US)

(72) Inventor: Brendan Jones, Ashland, OR (US)

(*) Notice: Subject to any disclaimer, the term of this patent is extended or adjusted under 35 U.S.C. 154(b) by 407 days.

(21) Appl. No.: 15/237,278

(22) Filed: Aug. 15, 2016

(65) Prior Publication Data

US 2017/0056607 A1 Mar. 2, 2017

Related U.S. Application Data

(60) Provisional application No. 62/210,640, filed on Aug. 27, 2015.

(51) Int. Cl.

| | |
|---|---|
| *A61M 15/06* | (2006.01) |
| *A61M 11/00* | (2006.01) |
| *A24D 3/00* | (2006.01) |
| *A61M 11/04* | (2006.01) |
| *A24F 1/30* | (2006.01) |
| *A24D 3/08* | (2006.01) |
| *A24F 47/00* | (2006.01) |

(Continued)

(52) U.S. Cl.

CPC ............ *A61M 11/003* (2014.02); *A24D 3/08* (2013.01); *A24F 1/30* (2013.01); *A24F 47/002* (2013.01);

(Continued)

(58) Field of Classification Search

CPC .......... A24C 5/472; A24D 1/02; A24D 1/045; A24D 3/04; A24D 3/041; A24D 3/048; A24F 1/30; A24F 13/06; A24F 47/006; A24F 47/008; A24F 7/02; A24F 7/04; A41D 13/1146; A61K 31/415; A61K 31/435; A61K 31/445; A61K 31/46; A61K 31/55; A61M 11/04; A61M 11/042; A61M 11/044; A61M 15/00; A61M 15/06;

(Continued)

(56) References Cited

U.S. PATENT DOCUMENTS 3,097,655 A    7/1963  Oden
3,375,920 A *  4/1968  Shaw ................ A24D 3/048
                                               131/331

(Continued)

FOREIGN PATENT DOCUMENTS

| CN | 201079005  | 7/2008 |
| FR | 2798826    | 3/2001 |
| WO | WO201476597 | 5/2014 |

*Primary Examiner* — Annette Dixon  
(74) *Attorney, Agent, or Firm* — Workman Nydegger (57) ABSTRACT

A system for filtering vaporized medicinal compounds includes a vaporizer configured to release one or more volatilized medicinal compounds in gaseous form, together with solid or semi-solid particulate byproducts, and one or more removable filters for efficiently removing at least a portion of the particulate byproducts while allowing passage of medicinally active volatilized compounds. The vaporizer includes a mouthpiece through which one or more volatilized medicinal compounds may be drawn. The filter is made of a chemically inert material (e.g., polypropylene or other polyolefin) and may be configured to detachably interface with an exposed surface of a vaporizer mouthpiece. The filter acts to remove solid or semi-solid particulate matter passing through the mouthpiece with minimal chemical and/or physical interference with volatilized medicinal compounds, which pass through the filter. The removable filter can also prevent cross-contamination by multiple users of the vaporizer.

21 Claims, 5 Drawing Sheets

(51) Int. Cl.
*A61K 36/185* (2006.01)
*A61M 15/00* (2006.01)

(52) U.S. Cl.
CPC .......... *A61K 36/185* (2013.01); *A61M 11/048* (2014.02); *A61M 15/0021* (2014.02); *A61M 2205/11* (2013.01); *A61M 2205/7545* (2013.01)

(58) Field of Classification Search
CPC ........ A61M 16/109; A61M 2016/0024; A61M 2205/8206; A62B 23/06; A63B 2071/088; A63B 71/085; B65D 81/052; C01F 7/142; C01F 7/38; C01G 23/047; C01G 49/06; C06B 47/00; C22B 1/02; C22B 21/0038; C22B 34/1209; C22B 34/1236; C22B 34/1259; C22B 5/10; C22B 7/04; E03B 2009/022; E03B 9/08; G01N 15/08; G01N 27/07; G01N 33/24; G02B 26/123; G02B 26/128; G02B 7/028; G06F 1/1626; G06F 1/1694; G06F 2200/1637; G06F 3/041; G06F 3/0488; G11C 11/4076; G11C 11/4091; G11C 2207/005; G11C 2207/2281; G11C 2207/229; G11C 7/065; H01H 2003/0293; H04M 2250/22; H04N 7/0112; H04N 7/012; Y02P 10/214; Y02P 10/218; Y02P 10/224; Y02P 10/23; Y10S 514/849
USPC ............ 128/201.18, 202.21, 202.27, 203.12, 128/203.26, 203.27, 204.13, 204.17, 128/204.21, 204.23, 204.29, 205.27, 128/206.12, 206.28, 206.29, 859
See application file for complete search history.

(56) References Cited

U.S. PATENT DOCUMENTS

| | | | | |
|---|---|---|---|---|
| 3,797,644 A | * | 3/1974 | Shaw | A24F 13/06 206/242 |
| 3,872,872 A | * | 3/1975 | Kahler | A24F 1/30 131/173 |
| 4,041,960 A | * | 8/1977 | Kahler | A24F 1/30 131/173 |
| 4,119,105 A | * | 10/1978 | Owens, Jr. | A24D 3/041 131/187 |
| 4,648,410 A | | 3/1987 | Seroussi | |
| 4,922,901 A | * | 5/1990 | Brooks | A24F 47/006 128/202.27 |
| 4,947,874 A | * | 8/1990 | Brooks | A24F 47/008 128/202.21 |
| 4,947,875 A | * | 8/1990 | Brooks | A24F 47/006 128/202.21 |
| 5,372,130 A | * | 12/1994 | Stern | A62B 18/006 128/205.25 |
| 5,603,317 A | * | 2/1997 | Farmer | A41D 13/1146 128/205.27 |
| 6,067,993 A | * | 5/2000 | Mahoney, III | A24F 1/30 131/173 |
| 6,250,301 B1 | | 6/2001 | Pate | |
| 8,534,296 B2 | | 9/2013 | Groff | |
| 8,955,521 B1 | * | 2/2015 | Hanson | A24F 1/00 131/191 |
| 8,973,585 B2 | | 3/2015 | Goldstein | |
| 2003/0209145 A1 | * | 11/2003 | Soper | A62B 23/06 95/273 |
| 2007/0151568 A1 | * | 7/2007 | Maurello | A63B 71/085 128/859 |
| 2009/0235939 A1 | * | 9/2009 | Gonsalves | A24D 1/14 131/191 |
| 2009/0258117 A1 | * | 10/2009 | Lee | A24F 1/32 426/104 |
| 2009/0288670 A1 | * | 11/2009 | Lee | A23G 3/56 131/330 |
| 2010/0206319 A1 | | 8/2010 | Gorski | |
| 2011/0079231 A1 | | 4/2011 | Borushek et al. | |
| 2011/0186064 A1 | | 8/2011 | Patel | |
| 2013/0199550 A1 | * | 8/2013 | Ono | A24C 5/472 131/280 |
| 2013/0269716 A1 | * | 10/2013 | Hoang | A24F 1/28 131/191 |
| 2014/0230832 A1 | | 8/2014 | Saliman | |
| 2017/0105447 A1 | * | 4/2017 | Gay | A24F 7/04 |

\* cited by examiner

MEDICINAL VAPOR FILTRATION SYSTEM

CROSS REFERENCE TO RELATED APPLICATION

This application claims the benefit of U.S. Provisional Patent Application No. 62/210,640, filed Aug. 27, 2015, the disclosure of which is incorporated herein in its entirety.

BACKGROUND

1. Technical Field

The present disclosure relates to filtration of medicinal vapors, more specifically filtration of medicinal vapors containing smoke particles, other particulate matter, tar, and one or more volatilized medicinal compounds.

2. Background and Relevant Art

Medicinal arts have evolved over millennia to treat various maladies and injuries. There are a plethora of pharmaceutical products available to treat everything from cancer, anxiety, or pain. Before individual compounds were isolated and associated with their beneficial effect, civilizations relied on natural products from which some modern drugs derive. For example, aspirin—or more accurately the active precursor to aspirin—has been appreciated historically and holistically as a component of willow tree bark. The beneficial effects of aspirin can be drawn from the willow tree bark if an individual imbibes a tea made from the bark or simply chews on the bark for an extended period of time. In modern times, aspirin has been purified away from the contaminants or other non-aspirin related compounds within willow tree bark and is readily available in tablet form and at various dosages in nearly every modern pharmacy around the world.

Regardless of the purity and availability of pharmaceutical products, some individuals choose holistic methods to treat ailments. In some instances, a natural product may be more readily available, or available at reduced price, compared to the analogous pharmaceutical product. In other instances, the individual may prefer using a natural product over swallowing a pill or injecting a purified substance. In some limited, the science behind holistic medicinal treatments has yet to be fully elucidated, giving the consumption and/or use of whole natural products an enigmatic benefit over modern pharmaceutical approaches.

Regardless of the rationale, holistic medicine and similar approaches where the whole natural product is used can be associated with certain risks. To obtain the desired benefit, the whole natural product is often consumed or used in the generation of a medicinal end product. Because these approaches do not rely on a finely purified product, there can be contaminants depending on the mode of administration. For example, individuals medicated with medicinal marijuana often receive the desired medicinal effect by smoking whole dried plant matter. In addition to producing volatilized medicinal compounds, burning dried plant matter also produces significant quantities of soot, ash, burning embers, and tar, which can be inhaled by the user. While cannabinoids have been received with greater acceptance as being generally safe and effective in treating a variety of ailments, there remains a major risk of inadvertently co-inhaling particulate materials in addition to the volatilized medicinal compounds of interest.

BRIEF SUMMARY

Implementations of the present disclosure comprise systems and methods for filtering smoke particles and other particulate matter from vaporized medicinal compounds. In particular, implementations of the present disclosure comprise systems and methods for utilizing a chemically inert filter to remove smoke particles and other particulate matter from volatilized medicinal compounds produced by the combustion of plant or other source material using a medicinal vaporizer, e.g., such as a pipe, water pipe, hookah, bong, or other smoking/combustion device. Additionally, implementations of the present disclosure can reduce cross-contamination between patients using a common medicinal vaporizer mouthpiece.

For example, systems and methods are provided that include a medicinal vaporizer configured to combust a source material and concomitantly produce volatilized medicinal compounds and undesirable smoke particles or other particulate matter, and wherein the one or more volatilized medicinal compounds in vapor form are inhaled using at least one mouthpiece. The systems and methods further include use of a filter comprised of a chemically inert material, wherein the filter is configured to cover a mouth-contacting surface of the mouthpiece and remove smoke particles or other particulate matter generated by the medicinal vaporizer and which pass through the mouthpiece. The filter is advantageously configured to minimize chemical and/or physical interaction with the volatilized medicinal compounds of interest passing through the filter while removing most or all smoke or other particulate matter.

In at least one embodiment of the present disclosure, the system for filtering particulate matter from a medicinal vapor may be applied in a group session. This may include one or more patients sharing the same medicinal vaporizer (i.e., smoking device) with each filtering the medical vapor to receive the desired volatilized medicinal compounds using their own personal, detachable filter, which removed smoke or other undesirable particles. Use of individual removable filters minimizes or prevents cross-contamination of the vaporizer mouthpiece among and between patients. In one embodiment, the volatilized medicinal compounds may include cannabinoids. Alternatively, or additionally, the volatilized medicinal compounds may include nicotine, an opioid, an analgesic compound, a stimulant, a narcotic, or a psychotropic compound.

Additional features and advantages of exemplary implementations of the disclosure will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Implementations of the present disclosure extend to systems and methods for filtering particulate matter from vaporized medicinal compounds. In particular, implementations of the present disclosure comprise systems and methods for utilizing an inert filter to remove particulate matter from volatilized medicinal compounds produced by a medicinal vaporizer, such as one that involves combustion of plant or other source material. Additionally, implementations of the present disclosure can reduce cross-contamination of a vaporizer mouthpiece between patients utilizing the same vaporizer in a group therapy setting.

Implementations of the present disclosure extend to systems to filter volatilized medicinal compounds that are produced by smoking medicinal marijuana. Further, implementations of the enclosed disclosure can promote a safer and more hygienic alternative to sharing a water or waterless pipe by multiple patients. The biggest cause of hospitalization from inhaling medicinal marijuana smoke is particulate inhalation, not inhalation of the beneficial medicinal cannabinoids. Inhalation of soot, burning marijuana embers, and "tar" (which is a complex mixture of oily semi-solid and/or solid hydrocarbons that can coat the lungs and cause significant damage to lung tissue) can be very harsh on the lungs and respiratory tract of patients generating and inhaling medicinal *cannabis* vapors for medicinal purposes. The systems and methods described herein make it possible to more easily, safely, and hygienically treat one or more patients with a regimen of medicinal marijuana using a single or multiple vaporizers.

As used herein, the terms "medicinal vaporizer" and "vaporizer" refer to smoking devices that produce volatilized medicinal oils or other vapors through the combustion of plant and/or other organic plant-derived or source matter. Typically, such combustion produces volatilized medicinal compounds together with undesirable particulate byproducts such as soot, burning embers, smoke, tar, and other unhealthy solids.

The term "medicinal vapor" refers to the product that is produced by a "vaporizer", including both the volatilized medicinal compounds and undesirable particulate matter or solids, which can be partially, mostly, or essentially entirely removed by filtration according to the disclosure.

Existing technologies are not well-equipped to efficiently filter undesired solids from volatilized medicinal compounds medicinal without also removing a substantial portion of the desired medicinal compounds. Traditional smoking filters, especially those used with tobacco products, reside either inside of a vaporizer/smoking device mouthpiece, are an elongated extension of a tube-like product (e.g., cigarette) to be smoked, and are made using chemically active materials. Filters that are elongated extensions of the tube-like products to be smoked are evidenced in traditional cigarettes, where the user inhales the smoke of burning tobacco through a cellulose- or cellulose acetate-based filter situated on an end proximate the user. Such filters typically range from 0.75 inches long to 1.25 inches long and are highly effective in adsorbing many dangerous chemical compounds drawn through them, including a portion of smoke particles and tar.

While traditional cellulose acetate cigarette filters can be used to filter burning medicinal marijuana, it has now been discovered that a substantial portion of desired volatilized oils (e.g., tetrahydrocannabinol (THC), cannabidiol (CBD), and other cannabinoids) are undesirably removed from the medicinal vapor before reaching the patient. THC, CBD and other desired cannabinoids are efficiently and readily absorbed by and retained in traditional cellulose and cellulose acetate filters due to the chemical nature of such materials. Such characteristics are very useful for filtering tobacco smoke, which contains thousands of undesired volatilized compounds in addition to nicotine. However, it has now been found that, in the case of marijuana based medicinal treatment, cellulose acetate filters are overly "efficient" in adsorbing and reducing the concentration of desired medicinal volatilized oils in the medicinal vapor. Similar problems exist for commercial filters found within mouthpieces of vaporizers/smoking devices such as hookah pipes, nargiles, and/or other water or waterless pipes. There is a delicate balance between filtering unwanted particulate matter from medicinal marijuana smoke while maximizing the total concentration of the desired medicinal volatilized oils generated from burning medicinal marijuana.

Heat generated by burning dried marijuana leaves or other source materials causes medicinally beneficial volatilized oils contained therein to be volatilized and available for inhalation for therapeutic value. The burning leaves or other source materials also emit soot, burning embers, tar, or other solid or semi-solid particulates that have no or negative therapeutic value and are therefore undesirable. However, when smoke, tar and volatilized oils of interest are passed through a chemically active filter, such as a traditional cigarette filter, a substantial amount of volatilized oils of interest can be adsorbed on and retained by the filter. Alternatively, even "inert" filters, if excessively long in the direction of the draw, can cool the medicinal vapor sufficiently to cause at least some of the volatilized compounds of interest to condense onto the interior surfaces of the filter, causing the filter to remove both undesired particulates and desired volatilized compounds of interest. It has now been discovered that the combination of chemical inertness and thin cross-section provides the dual benefit of efficient filtration of particulate matter while permitting most or a substantial majority of volatilized medicinal compounds of interest to pass through the filter.

Further, patients in a group setting often share a single vaporizer/smoking device. This can pose a serious risk of cross-contamination of the mouthpiece surface of the vaporizer with orally communicable diseases or ailments between members of the group. Traditional filtration devices do not address this health issue. Therefore, the inert filters disclosed herein can be advantageously removable and designed for single or limited use, with each member of a group having an assigned removable filter.

Implementations of the present disclosure alleviate many if not all of the aforementioned potential negative consequences associated with current filtration systems. Many implementations are likely to significantly decrease the quantity of undesired particulate matter produced by a vaporizer/smoking device without unnecessarily removing too much of the volatilized oils or compounds of interest. Additionally, implementations of the present disclosure may protect patients from cross-contamination of a shared vaporizer.

Figure 1:
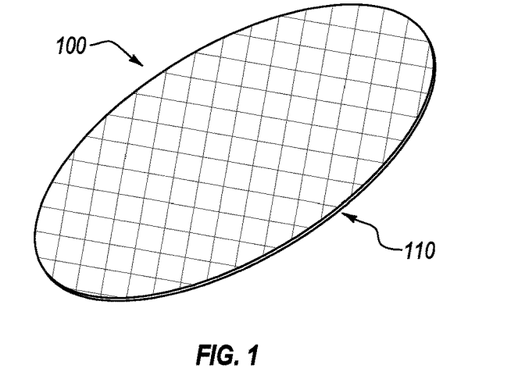
FIG. 1 illustrates a schematic representation of a chemically inert filter according to one implementation of the present disclosure.

By way of example, illustrated in FIG. 1 is a schematic representation of an inert filter 100 according to one implementation of the present disclosure. The inert filter 100 may be made partially or entirely of an inert polymer. As a non-limiting example, the inert polymer comprising inert filter 100 may be polypropylene or other polyolefin. Inert filters 100 made from polypropylene—or other similar inert polymers and compounds—may offer certain advantages. For example, the chemical properties of polypropylene that give it an inert quality—that does not readily chemically react with other compounds at standard temperature and pressure—may allow volatilized oils to pass through the filter without substantial chemical interaction and/or physical adsorption. In contrast, cellulose and cellulose acetate based filters are not inert but contain polar oxygen groups that can bind to certain organic compounds, including heteroatoms contained in cannabinoids.

While inert filter 100 may be constructed of an inert compound such as polypropylene and not chemically react with chemical compounds passing through the filter, it nonetheless acts as a physical filter for removing particulate matter, such as smoke and other solid particles, tar, and other solid or semi-solid contaminants. Accordingly, solid or semi-solid contaminants contained in smoke—such as smoke produced by burning medicinal marijuana—may include soot, embers, leaf particulate, ash, and/or tar, and the inert filter 100, while not acting as a chemical filter, may nonetheless act as a physical barrier to the passage of the foregoing solid or semi-solid contaminants through the inert filter 100. Therefore, the inert filter 100 may, in one embodiment, act to physically filter solid or semi-solid contaminants found in medicinal marijuana smoke while allowing a major portion of volatilized cannabinoid compounds of interest to pass through unhindered. In another embodiment, the inert filter 100 may act to physically filter solid or semi-solid contaminants associated with other medicinal vapors containing other compounds of interest, such as opioids, analgesic compounds, stimulants, narcotics, psychotropic compounds, and even nicotine.

In addition to inert filter 100 not chemically interfering with volatilized organic compounds and/or oils of interest, inert filter 100 may, in one embodiment and as illustrated in FIG. 1, be made of single layer and/or have a thin profile (i.e., short draw pathway). The cross-sectional thickness 110 of a filter may influence the total concentration of gaseous volatilized oils that become bound to the filter. Gaseous volatilized oils that enter a filter do so with a certain amount of heat energy, which contributes to the volatilized oil remaining in a gaseous state. As the gaseous volatilized oil traverses a filter, heat dissipates to the surrounding environment. If enough heat is lost, the gaseous volatilized oil may undergo a phase change and condense onto the inner surface of the filter.

To effectively filter solid or semi-solid contaminants without unnecessarily removing volatilized compounds of interest, the cross-sectional thickness of inert filter 100 can be in a range from about 0.001 inch to about 0.25 inch. In another embodiment, the cross-sectional thickness is between about 0.13 inch and about 0.75 inch. In a preferred embodiment, the cross-sectional thickness of the inert filter 100 is between about 0.005 inch and 0.1 inch. In a more preferred embodiment, the thickness of the inert filter 100 is between 0.008 inch and 0.025 inch. In one embodiment, multiple inert filters 100 may be stacked upon one another to selectively increase the thickness filtration of solid or semi-solid contaminants.

With continued reference to FIG. 1, the inert filter 100 may, in one embodiment, be substantially flat and flexible. As a non-limiting example, the inert filter 100 may have a uniform or substantially uniform thickness. The inert filter 100 may, in the same or further embodiments, be flexible. For example, the flexibility of inert filter 100 may allow the inert filter 100 to be substantially bent and/or flexed along one or more three dimensional axes without, ripping, tearing, breaking, or otherwise compromising the integrity and functionality of the inert filter 100. This permits the filter to be wrapped around a vaporizer mouthpiece during use. In one embodiment, the inert filter is substantially flat and flexible and comprises polypropylene.

While the inert filter 100 of FIG. 1 is depicted as being circular and/or elliptical, the filter can assume other shapes as desired. As a non-limiting example, an inert filter 100 may be polygonal (e.g., shaped like a triangle, quadrilateral, pentagon, or other multi-sided shape). As a further non-limiting example, the inert filter 100 may be shaped like a symbol such as a star or sun. Another non-limiting example may include the inert filter 100 shaped like an animal such as a fish, bear, or dragon. In one embodiment, the inert filter 100 may be pre-formed and/or folded into a shape that would fit and/or slide over a mouthpiece of a vaporizer. Regardless of the shape of inert filter 100, the flexibility of the inert filter 100 may not be affected.

Figure 2A:
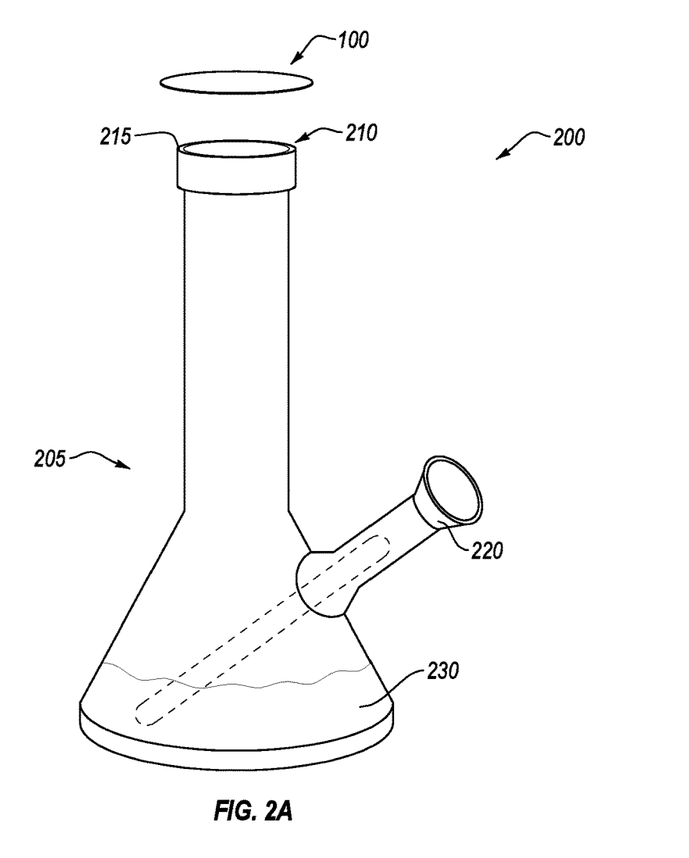
FIG. 2A illustrates an exemplary system for filtering particulate matter from volatilized medicinal compounds according to one implementation of the present disclosure.

Referring to FIG. 2A, illustrated is a system 200 for filtering solid or semi-solid contaminants from volatilized medicinal compounds in a medicinal vapor. As illustrated in FIG. 2A, said system includes a medicinal vaporizer 205 (e.g., smoking device) configured to release one or more volatilized medicinal compounds in a gaseous form and produce solid or semi-solid byproducts. The vaporizer 205 may include a mouthpiece 210 through which the medical vapor is drawn by the mouth of a user (e.g., by inhaling, puffing or cheek suctioning). Mouthpiece 210 therefore includes a distal opening and a mouth-contacting surface 215. System 200 additionally includes an inert filter 100 comprised of a chemically inert material. The inert filter 100 may be configured to removably cover mouth-contacting surface 215 of the mouthpiece 210 and may act to remove particulate matter passing through the mouthpiece 210 without chemically interfering with the one or more volatilized medicinal compounds passing through the inert filter 100.

Illustrated in FIG. 2A, the medicinal vaporizer 205 includes a lighting element 220. The lighting element 220 may be used as a combustion chamber for combusting plant, plant-derived matter and/or other source material in order to generate volatilized medicinal compounds in a medicinal vapor containing solid or semi-contaminants as byproduct. In one embodiment, the lighting element may be used to burn medicinal marijuana, the heat of which releases gaseous volatilized cannabinoids into vaporizer 205. In another embodiment, the lighting element 220 may be a nebulizing element for medicinal compounds, which may include volatilized organic medicinal oils. The medicinal vaporizer 205 also produces solid or semi-solid contaminant byproducts to be filtered out using the disclosed filter.

The vaporizer 205 illustrated in FIG. 2A is depicted as a water pipe smoking device having water 230 within the base of vaporizer 205 that may be used as a rudimentary pre-filter for smoke emanating from lighting element 220. Air drawn through the vaporizer 205 may pull air through the lighting element 220 and consequently through the water 230, causing a bubbling effect as the air is introduced into the water. The bubbles rise through the water 230 and break, releasing smoke and volatilized oils into a chamber that is directly or indirectly associated with mouthpiece 210 of vaporizer 205. The water 230 may, in alternative embodiments, be located at various locations within vaporizer 205 but may serve the same or substantially similar function as a rudimentary pre-filter to quench burning embers and remove heavier particles.

In one embodiment, and similar to that depicted in FIG. 2A, smoke passing through water 230 may be further filtered as it passes through inert filter 100 associated with mouthpiece 210. In one embodiment, the smoke may be smoke generated from the burning of medicinal marijuana, and the water 230 may act to remove large leaf particles and/or other particles and debris caught in the water, including soot, embers, and ash. The pre-filtered smoke rising from the water may then be subject to the finer filtration of inert filter 100, the inert filter 100 allowing passage of one or more volatilized medicinal compounds of interest while removing solid or semi-solid contaminants. In an embodiment where medicinal marijuana is used, the one or more volatilized medicinal compounds may include THC, CBD, and other volatilized cannabinoids. In other embodiments, the one or more volatilized medicinal compounds may include one or more opioids, one or more analgesic compounds, one or more psychotropic compounds, one or more stimulants, one or more narcotics, or even nicotine.

Regardless of the specific type of one or more volatilized medicinal compounds, the inert filter 100 may allow passage of a majority of total volatilized medicinal compounds. In one embodiment, the inert filter 100 permits passage of at least 75% of the one or more volatilized medicinal compounds. In another embodiment, the inert filter 100 permits passage of at least 85% of the one or more volatilized medicinal compounds. In a preferred embodiment, the inert filter 100 permits passage of at least 95% of the one or more volatilized medicinal compounds. In a more preferred embodiment, the inert filter 100 permits passage of at least 99% of the one or more volatilized medicinal compounds.

Figure 2B:
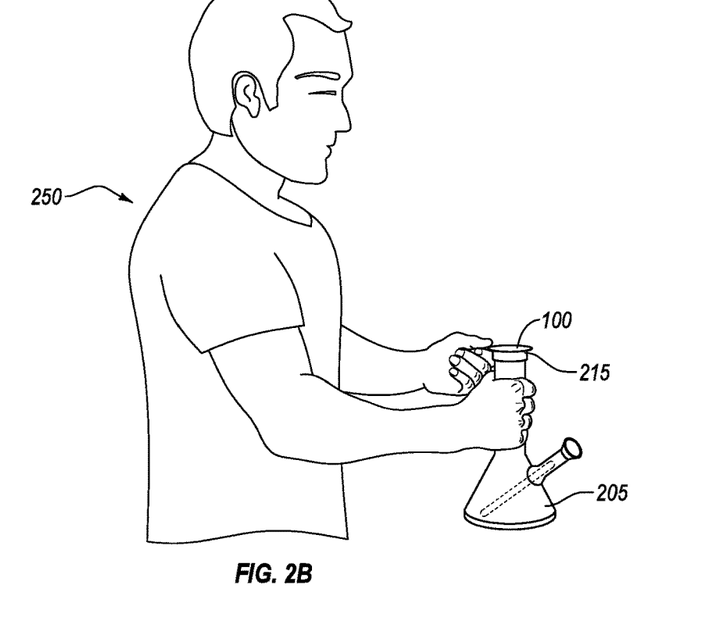
FIGS. 2B-C illustrate an exemplary use of a vaporizer by a patient according to one implementation of the present disclosure.
Figure 2C:
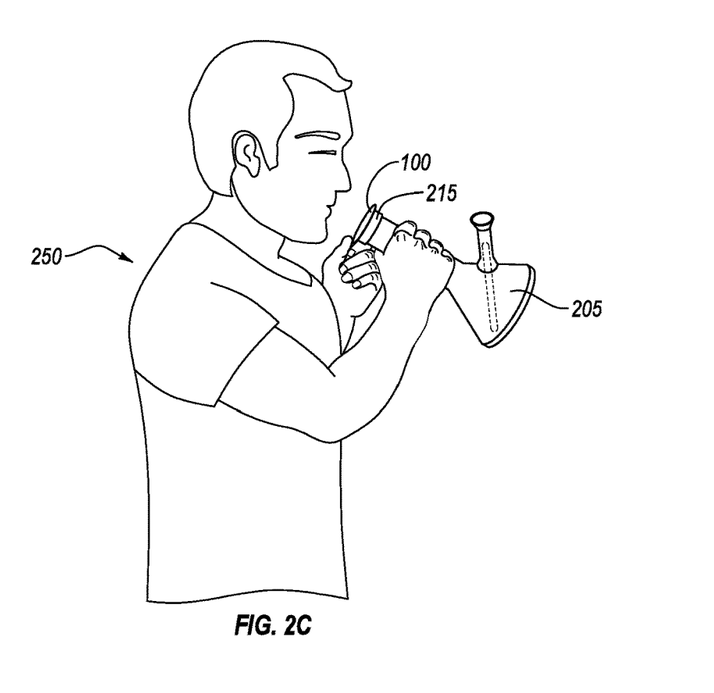

Referring now to FIGS. 2B and 2C, illustrated is a patient 250 utilizing a personal, inert filter 100 in conjunction with vaporizer/smoking device 205. More specifically, FIGS. 2B-2C illustrate a method for a patient 250 to remove solid and semi-solid contaminants from one or more volatilized medicinal compounds of interest in medicinal vapor produced by vaporizer 205. As illustrated in FIG. 2B, the patient 250 may removably apply an inert filter 100 over a mouth-contacting surface 215 of a vaporizer 205. The inert filter 100 may act as a temporary barrier between an interior portion of the vaporizer 205 configured to contain one or more volatilized medicinal compounds and an exterior environment such that when the vaporizer 205 is engaged by patient 250, the patient 250 interfaces with the vaporizer 205 through the inert filter 100 and does not directly contact the mouth-contacting surface 215 of the vaporizer 205. A pressure differential (e.g., suction) may be applied to the interior portion of the vaporizer 205 sufficient to cause the one or more volatilized medicinal compounds to pass through the inert filter to the exterior environment and/or to the patient 250, the one or more volatilized medicinal compounds being chemically non-reactive with the inert filter 100 and solid and/or semi-solid particulate matter being trapped on or within the inert filter 100.

In one embodiment, the inert filter 100 is compressed upon the mouth-contacting surface 215 of the vaporizer 205 by the patient 250 such that, while still removably connected to the vaporizer 205, substantially all of the one or more volatilized medical compounds may either pass through inert filter 100 or are otherwise held within the vaporizer 205 for later user. The inert filter 100 may be configured to interface with the mouthpiece 210 and may completely cover the mouth-contacting surface 215 of the vaporizer 205 such that when a patient interfaces with the vaporizer 205 through the inert filter 100, the patient's mouth does not come into direct contact with the mouth-contacting surface 215 of the vaporizer 205, generally, and/or the mouthpiece 210, specifically. In another embodiment, the inert filter 100 is compressed upon the mouth-contacting surface 215 of the vaporizer 205 by a device that securely attaches to the mouth-contacting surface 215 of the vaporizer. In such an embodiment, the device may be removed from the vaporizer so that the inert filter 100 may be removed, added upon, or adjusted.

In one embodiment, the differential pressure applied to the interior portion of the vaporizer 205 may be a negative pressure that is applied through the inert filter 100, originating from the external environment. In one embodiment, and as depicted in FIG. 2C, the pressure applied to the vaporizer 205 may be negative generated by a patient 250. The patient's inhalation may force the volatilized medicinal compounds within the vaporizer 205 to transmit though the inert filter 100 and into the patient for medicinal benefit. In another embodiment, the pressure applied to the vaporizer may be positive pressure generated from within the vaporizer 205 or from an external source forcing air and/or pressure into the vaporizer 205. When positive pressure is applied to the vaporizer 205 at a point other than at the mouthpiece 210, a point of egress for the internally forced air may be through the mouthpiece 210 covered by an inert filter 100. In one embodiment, the positive pressure may be applied at the lighting element 220 or another point distal to the mouthpiece 210.

Figure 3A:
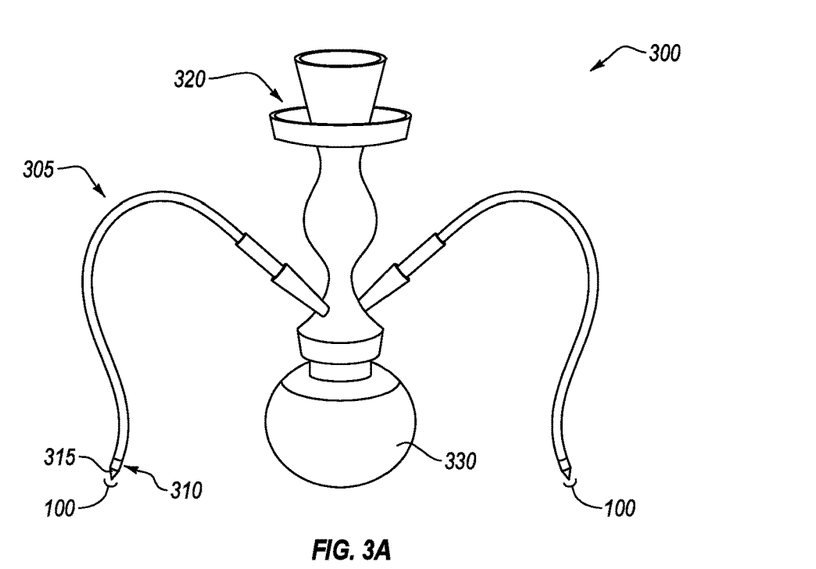
FIG. 3A illustrates an exemplary vaporizer according to one implementation of the present disclosure.

Referring now to FIG. 3A, illustrated is a system 300 for filtering solid or semi-solid particulate material from vaporized medicinal compounds. The system 300 may be functionally similar to the filtration system 200 previously described. Certain features of system 300 will not be described in relation to this embodiment wherein those components may function in the manner as described above in FIG. 2A and are hereby incorporated into this embodiment. Like structures and/or components are given like reference numerals.

The system 300 may include one or more mouthpieces 310 connected to or otherwise associated with a vaporizer (e.g., smoking device) 305. The vaporizer 305 may be configured to release one or more volatilized medicinal compounds in a gaseous form through the one or more mouthpieces 310. In one embodiment, medicinal marijuana is placed in the lighting portion 320 of the vaporizer 305, and the smoke from the burning medicinal marijuana is drawn through the water 330 found within vaporizer 305, providing a similar filtration effect as observed with certain embodiments of vaporizer 205. The smoke drawn through the water 330 may then be inhaled for medicinal purposes through mouthpiece(s) 310. In one embodiment, the vaporizer 305 may be a hookah, water pipe or bong. In another embodiment, the vaporizer 305 may be a nargile, tobacco water pipe, or other water pipe.

Figure 3B:
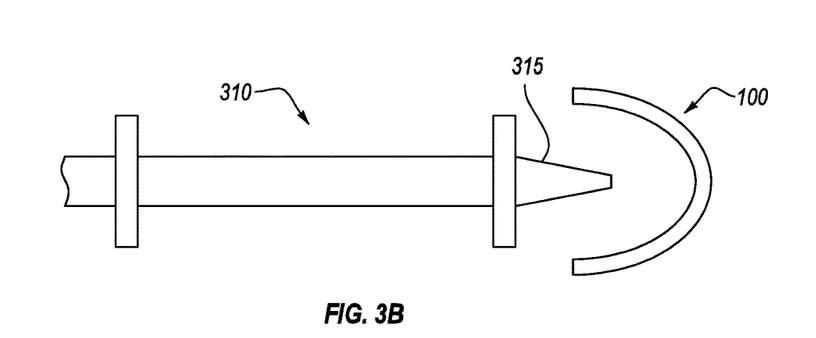
FIG. 3B illustrates a schematic view of a mouthpiece from the exemplary vaporizer illustrated in FIG. 3A and an inert filter according to one implementation of the present disclosure.

In one embodiment, and as illustrated in FIG. 3A, the vaporizer 305 may have two mouthpieces 310 such that multiple users may draw and receive medicinal vapors from the same medical device. For example, two users may simultaneously use vaporizer 305 depicted in FIG. 3 without interfering with each other's usage. Such concurrent use may be beneficial to maximize the efficiency of medicinal product utilized in addition to providing opportunities for users to socialize and share their experience during prolonged treatment regimens.

In one embodiment, and as illustrated in FIG. 3A, each mouthpiece 310 of vaporizer 305 may be individually associated with an inert filter 100. With continued reference to FIG. 3A, but also referencing FIG. 3B for additional clarification, each inert filter 100 may conform to the oral administration surface 315 of mouthpiece 310. The inert filter 100 may be, in some embodiments, flexible such that when the patient engages the vaporizer 305 through the mouthpiece 310, the inert filter 100 substantially covers at least a portion of the mouth-contacting surface 315. In this manner, the patient 250 utilizing the vaporizer 305 does not have to make direct contact with their mouth and mouthpiece 310. The inert filter 100 may act as a barrier to the patient and mouthpiece 310 while simultaneously acting as a filter to separate a substantial portion of solid or semi-solid particulate matter from the one or more volatilized medicinal compounds of interest produced by vaporizer 305.

In one embodiment, vaporizer 305 may have more than two mouthpieces 310 associated with it. While additional mouthpieces 310 may be utilized for vaporizer 305 to increase the total number of users that can use vaporizer 305, a single mouthpiece 310 may additionally or alternatively be used by multiple users. For example, a single mouthpiece 310 may be used by more than one user having their own, individual inert filter 100 to be applied and used with the mouthpiece 310 to sequentially or periodically receive a dose of one or more volatilized medicinal compounds. The individual inert filters 100 may be exchanged by a patients, medical staff, or machines in between each separate patient's interaction with mouthpiece 310. As a further example, multiple patients may use the same inert filter 100, which can be exchanged at the end of their collective treatment period at mouthpiece 310.

In one embodiment, the inert filter 100 is detachably attached to the mouthpiece 310 but still allows for the patient 250 to have mostly unimpeded access and interface with the mouth-contacting surface 315. The inert filter 100 may still act to filter particulate matter from the one or more volatilized medicinal compounds. In one embodiment, the inert filter 100 is shaped to securely, yet detachably, fit to mouthpiece 310.

Figure 4:
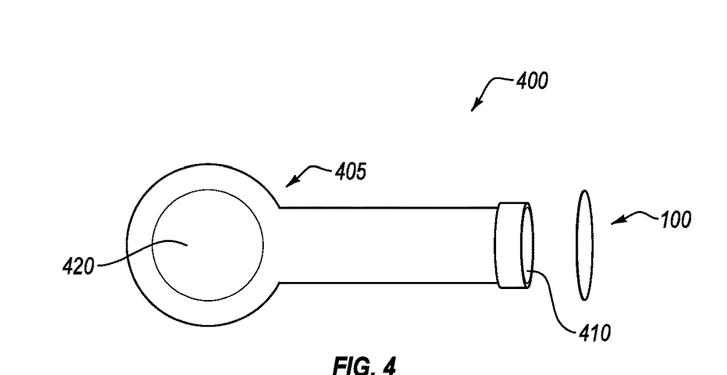
FIG. 4 illustrates a waterless system for filtering particulate matter from volatilized medicinal compounds according to one implementation of the present disclosure.

Illustrated in FIG. 4 is a system 400 for filtering vaporized medicinal compounds. The system 400 may be functionally similar to the filtration system 200 previously described. Certain features of system 300 will not be described in relation to this embodiment wherein those components may function in the manner as described above in FIGS. 2A and 3A and are hereby incorporated into this embodiment. Like structures and/or components are given like reference numerals.

The system 400 may include one or more mouthpieces 410 connected to or otherwise associated with a vaporizer 405, the vaporizer 405 may be configured to release one or more volatilized medicinal compounds in a gaseous form through the one or more mouthpieces 410. In one embodiment, medicinal marijuana is placed in the lighting portion 420 of the vaporizer 405, and the smoke from the burning medicinal marijuana is drawn through the vaporizer 405 to the mouthpiece(s) 410 and through the inert filter 100. In one embodiment, the vaporizer 405 may be glass spoon pipe. In another embodiment, the vaporizer 405 may be a wooden tobacco pipe, cork pipe, acrylic pipe, stone pipe, or other waterless pipe.

Figure 5:
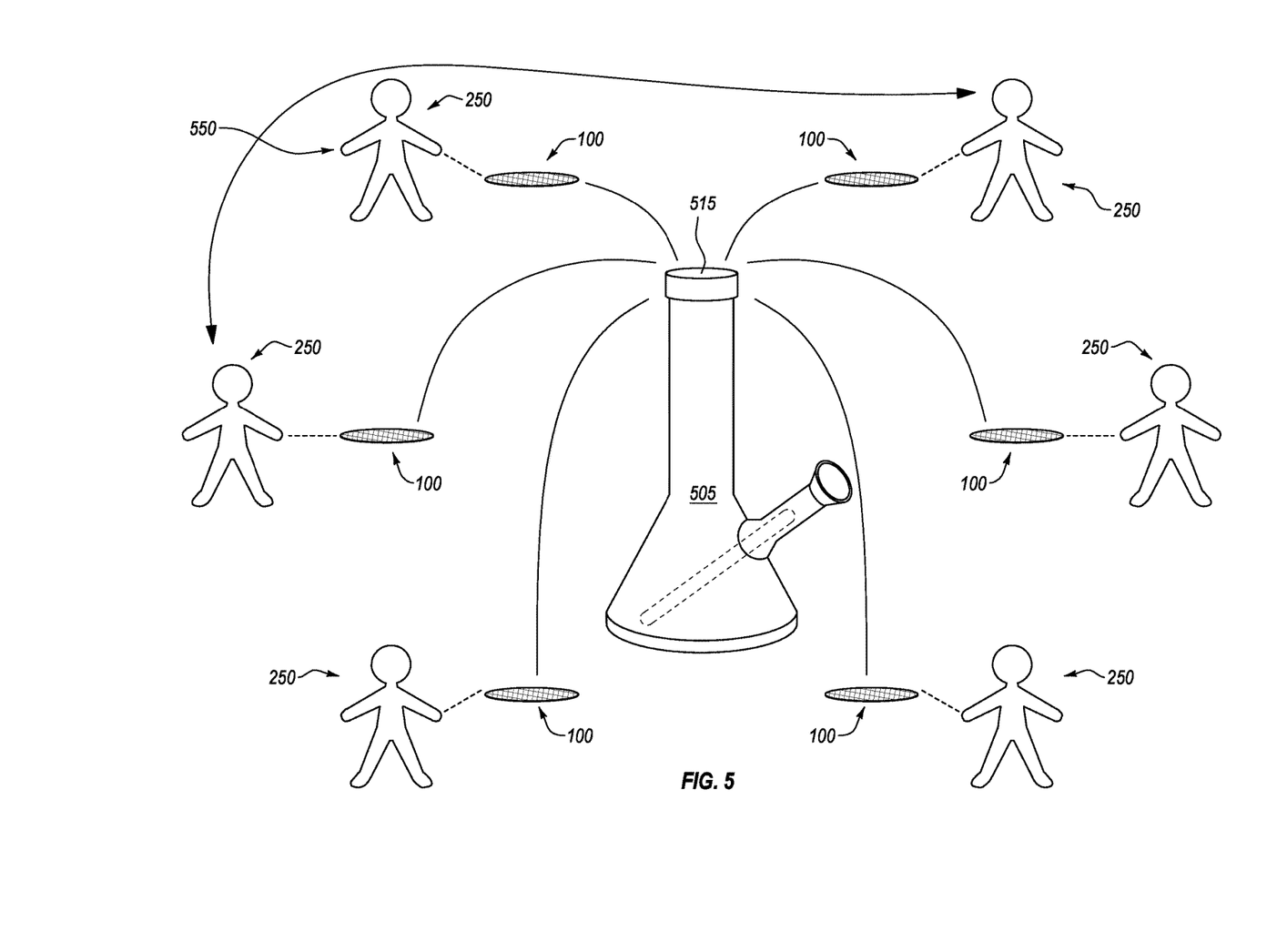
FIG. 5 illustrates a schematic representation of a single vaporizing used in a group patient therapy setting according to implementations of the present disclosure.

With reference to FIG. 5, illustrated is a schematic of a vaporized *cannabis* treatment regimen to a group of patients 550 sharing a single vaporizer 505. In one embodiment, cross-contamination of the vaporizer 505 by individual patients 250 is minimized or eliminated through the use of patient-specific oral inert filters 100. Each patient 250 in the group of patients 550 may detachably apply one or more inert filters 100 over a mouth-contacting surface 515 of a vaporizer 505. Each of the one or more inert filters 100 may act as a temporary partition between an interior portion of the vaporizer 505 and an exterior environment and may be configured to contain one or more volatilized cannabinoid compounds within the interior portion of the vaporizer 505. In one embodiment, the vaporizer 505 is engaged by a patient 250 through the one or more inert filters 100, and in doing so, the patient 250 does not directly contact the mouth-contacting surface 515 of the vaporizer 505.

With continued reference to FIG. 5, a patient 250 may apply differential pressure to the interior portion of the vaporizer sufficient to cause one or more volatilized cannabinoid compounds to pass through the one or more inert filters 100 used by the patient 250. The one or more volatilized cannabinoid compounds may be chemically non-reactive with the one or more patient-specific inert filters 100 and may act to trap solid or semi-solid particulate matter on or within the one or more patient-specific inert filters 100. A patient 250 may remove the one or more patient-specific inert filters 100 from the mouth-contacting surface 515 of the vaporizer 505 upon receipt of a medicinal dose from the vaporizer 505 and pass the vaporizer 505 to another patient 250 within the group of patients 550.

As a non-limiting example, inert filters 100 may be distributed to each patient 250 in a group setting, and each patient 250 can place his or her own personal, inert filter 100 to cover the mouth-contacting surface 515 of a water pipe without cross-contaminating others or receiving contamination from others. The inert filters 100 may be easily placed over the mouth-contacting surface 515 while the individual patient 250 uses the water pipe and then subsequently removed so the next patient 250 may place his or her own inert filter 100 over the mouth-contacting surface 515 and receive a dosage of medicinal treatment. This may speed up the process of hygienic group therapy by not having to sanitize or disassemble the medical delivery device beach time it is used by a different patient 250.

Figure 6A:
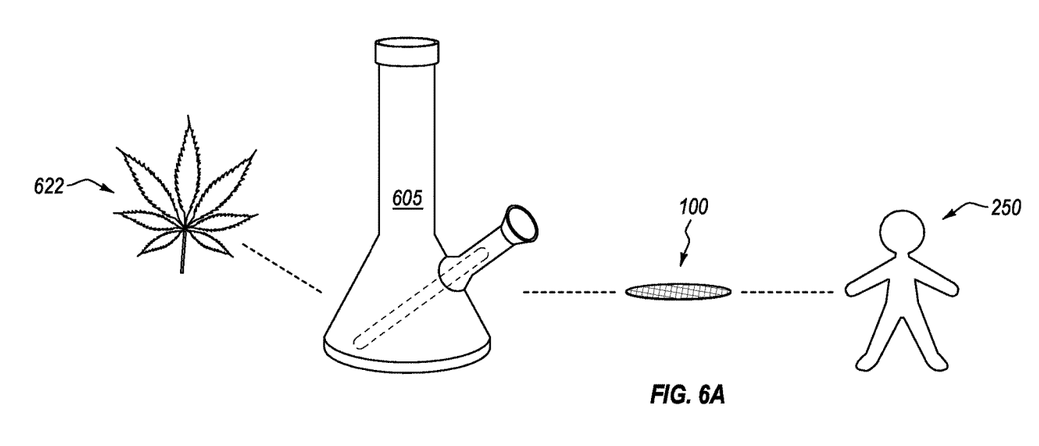
FIG. 6A illustrates a schematic representation of a system for filtering volatilized medicinal compounds derived from *cannabis*.
Figure 6B:
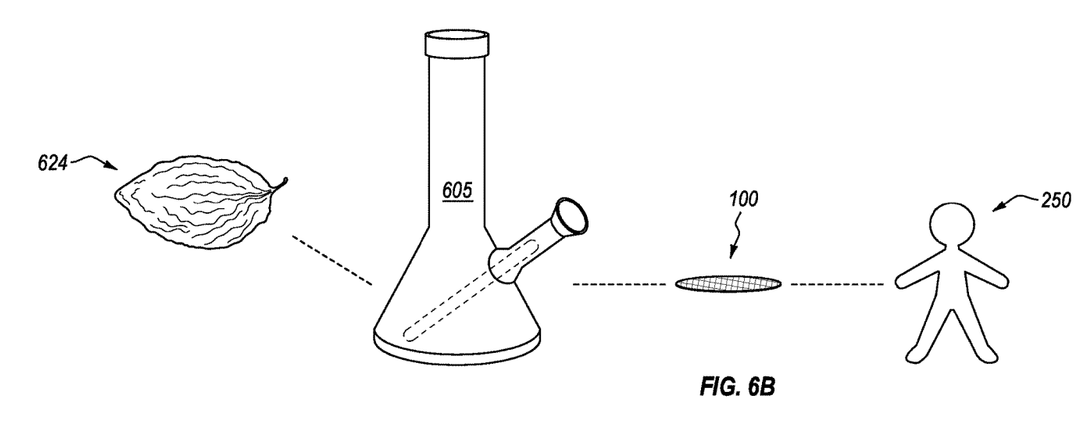
FIG. 6B illustrates a schematic representation of a system for filtering volatilized medicinal compounds derived from tobacco.

Referring now to FIG. 6A, illustrated is a vaporizer 605 that may be used by a patient 250 together with inert filter 100 during a treatment regimen requiring use of medicinal marijuana 622. FIG. 6B illustrates a vaporizer 605 that may be used by a patient 250 together with inert filter 100 during a treatment regimen requiring the use of tobacco 624. In one embodiment consistent with FIG. 6B, the vaporizer 605 and inert filter 100 may be used recreationally for the smoking of tobacco 624 and tobacco-related products.

Comparative Testing

Below is a specific example of compositions and methods which have been created according to the present invention.

Example 1

An inert filter 100 in accordance with the present invention was prepared and tested with the following properties:

| Properties | Description |
| --- | --- |
| Raw material | 100% polypropylene |
| Weight | 0.885 ounce/sqyard |
| Thickness | 11 mils |
| Tensile strength (machine direction) | 2.929 pounds/inch |
| Tensile strength (cross direction) | 2.25 pounds/inch |
| Elongation at break (machine direction) | 40% |
| Elongation at break (cross direction) | 60% |

An inert filter 100 with the properties described in the table above was tested for filtration of *cannabis* smoke to determine how many dosages (or "hits") were required to obtain the desired medicinal effect. When the term "hits" is used herein, it references inhalation of the medicinal vapor by a patient through the medical device that has vaporized the one or more medicinal cannabinoids of interest. Through reiterative testing it was determined that, on average, filtering the *cannabis*-based smoke through the inert filter above resulted in the patient obtaining the desired medicinal effects of the inhaled medical marijuana after only one to two hits.

In contrast, the same medicinal marijuana was used by the vaporizer but the smoke was filtered through a traditional cellulose acetate based cigarette filter. Through reiterative testing it was determined that a typical patient required six (6) to ten (10) hits to obtain the desired medicinal benefits from medical marijuana. Therefore, the inert filter used according to the disclosed invention permitted more efficient utilization of a bolus of medical marijuana while still removing the solid or semi-solid particulate matter to the same degree as the cigarette filter. This is surprising and unexpected. Accordingly, the inventive methods and systems of filtering medical marijuana smoke can simultaneously minimize inhalation of solid or semi-solid particulate contaminants while maximizing the availability of the volatilized medicinal compounds of interest.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of filtering solid and/or semi-solid particulate matter from a medicinal vapor, comprising:
providing a filter having a filter structure that is initially flat and flexible; providing a vaporizer that is a smoking device suitable for burning a plant or plant-derived material, wherein burning the plant or plant-derived material produces a medicinal vapor comprising one or more volatilized medicinal compounds and solid and/or semi-solid particulate matter selected from soot, embers, ash, and/or tar; removably
applying the filter over a distal opening and mouth-contacting surface of a mouthpiece of the vaporizer so that the filter covers the distal opening and is wrapped around the mouth-contacting surface of the mouthpiece; burning the plant or plant-derived material and forming
a medicinal vapor in the vaporizer, the medicinal vapor comprising one or more volatilized medicinal compounds and solid and/or semi-solid particulate matter selected from soot, embers, ash, and/or tar; passing the medicinal vapor through the mouthpiece and through the filter; and
the filter removing at least a portion of the solid and/or semi-solid particulate matter from the medicinal vapor while permitting a majority of the one or more volatilized medicinal compounds in the medicinal vapor to pass through the filter.

2. The method of claim 1, wherein removably applying the filter comprises a user covering the distal opening, wrapping the filter around the mouth-contacting surface of the mouthpiece, and holding the filter in place against the mouth-contacting surface.

3. The method of claim 1, wherein the filter is comprised of an inert material.

4. The method of claim 3, wherein the inert material comprises polypropylene.

5. The method of claim 1, wherein forming the medicinal vapor comprises forming one or more volatilized medicinal compounds comprising one or more cannabinoids.

6. The method of claim 1, wherein forming the medicinal vapor comprises forming one or more volatilized medicinal compounds comprising an opioid, an analgesic compound, a psychotropic compound, a narcotic, a stimulant, or nicotine.

7. The method of claim 1, the filter permitting passage of at least 75% of the one or more volatilized medicinal compounds produced by the vaporizer.

8. The method of claim 1, the filter permitting passage of at least 85% of the one or more volatilized medicinal compounds produced by the vaporizer.

9. The method of claim 1, the filter permitting passage of at least 95% of the one or more volatilized medicinal compounds produced by the vaporizer.

10. The method of claim 1, wherein the filter provides a sanitary barrier between a user's mouth and the mouth-contacting surface of the mouthpiece.

11. The method of claim 10, wherein the vaporizer is used by multiple users, each user having a personal filter, removably applying the personal filter to the mouthpiece prior to use, and holding the personal filter in place against the mouthpiece while drawing medicinal vapor through the filter.

12. The method of claim 1, wherein the vaporizer is a water-containing smoking device.

13. The method of claim 1, wherein the vaporizer is a waterless smoking device.

14. The method of claim 1, wherein the filter has a thickness in a range of 0.001 inch and 0.25 inch.

15. The method of claim 1, wherein the filter has a thickness in a range of 0.005 inch and 0.1 inch.

16. The method of claim 1, wherein the filter has a thickness in a range of 0.008 inch and 0.025 inch.

17. A method of oral administration of cannabinoid vapor to a group of users sharing a single vaporizer while minimizing or preventing cross-contamination of the vaporizer, comprising:

providing a plurality of filters, each having a filter structure that is initially flat and flexible; providing a vaporizer that is a smoking device suitable for burning a plant or plant-derived material, wherein burning the plant or plant-derived material produces a medicinal vapor comprising one or more volatilized medicinal compounds and solid and/or semi-solid particulate matter selected from soot, embers, ash, and/or tar; removably applying a first filter over a distal opening and mouth-contacting surface of a mouthpiece of the vaporizer so that the first filter covers the distal opening and is wrapped around the mouth-contacting surface of the mouthpiece; burning the plant or plant-derived material and forming a medicinal vapor in the vaporizer, the medicinal vapor comprising one or more volatilized cannabinoid compounds and solid or semi-solid particulate matter selected from soot, embers, ash, and/or tar; a first user drawing the medicinal vapor through the mouthpiece and the first filter;

removing the first filter from the mouthpiece of the vaporizer;

removably applying a second filter over the distal opening and mouth-contacting surface of the mouthpiece so that the second filter covers the distal opening and is wrapped around the mouth-contacting surface of the mouthpiece; and a second user drawing the medicinal vapor through the mouthpiece and the second filter, the first and second filters each filtering at least a portion of the solid or semi-solid particulate matter from the medicinal vapor, permitting a majority of the one or more volatilized cannabinoid compounds to pass through the filters, and minimizing or preventing cross-contamination of the vaporizer by the first and second users.

18. The method of claim 17, wherein the vaporizer is a water-containing smoking device.

19. The method of claim 17, wherein the vaporizer is a waterless smoking device.

20. The method of claim 17, wherein the filter has a thickness in a range of 0.001 inch and 0.25 inch.

21. The method of claim 17, wherein the filter has a thickness in a range of 0.005 inch and 0.1 inch.

* * * * *